(12) United States Patent
Meixueiro-Montes-De-Oca

(10) Patent No.: US 11,406,636 B2
(45) Date of Patent: Aug. 9, 2022

(54) COMBINED PHARMACEUTICAL COMPOSITION

(71) Applicant: Alepharma, Sociedad Anónima Promotora de inversión de Capital Variable, Mexico City (MX)

(72) Inventor: Juan Raúl Meixueiro-Montes-De-Oca, Mexico City (MX)

(73) Assignee: GIDD COMMERCIAL USA, INC., Eagle Pass, TX (US)

( * ) Notice: Subject to any disclaimer, the term of this patent is extended or adjusted under 35 U.S.C. 154(b) by 150 days.

(21) Appl. No.: 16/108,239

(22) Filed: Aug. 22, 2018

(65) Prior Publication Data
US 2019/0183892 A1    Jun. 20, 2019

(30) Foreign Application Priority Data
Dec. 19, 2017    (MX) .................... MX/a/2017/016719

(51) Int. Cl.
| | |
|---|---|
| A61K 31/51 | (2006.01) |
| A61P 25/02 | (2006.01) |
| A61P 27/02 | (2006.01) |
| A61K 9/00 | (2006.01) |
| A61K 9/20 | (2006.01) |
| A61K 9/48 | (2006.01) |
| A61K 31/7048 | (2006.01) |
| A61K 31/4415 | (2006.01) |
| A61K 31/353 | (2006.01) |
| A61K 31/12 | (2006.01) |

(52) U.S. Cl.
CPC ............ *A61K 31/51* (2013.01); *A61K 9/0019* (2013.01); *A61K 9/0053* (2013.01); *A61K 9/20* (2013.01); *A61K 9/48* (2013.01); *A61P 25/02* (2018.01); *A61P 27/02* (2018.01); *A61K 31/12* (2013.01); *A61K 31/353* (2013.01); *A61K 31/4415* (2013.01); *A61K 31/7048* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 2007/0059378 A1* | 3/2007 | Bland | ................... | A61K 31/197 424/601 |
| 2008/0044390 A1* | 2/2008 | Jin | ....................... | A61K 31/352 424/93.7 |
| 2008/0057115 A1* | 3/2008 | Okamoto | ................... | A61P 9/10 424/452 |
| 2013/0071525 A1* | 3/2013 | Kanaya | ................... | A23D 9/007 426/99 |

FOREIGN PATENT DOCUMENTS

WO    2016/179097 A1    11/2016

OTHER PUBLICATIONS

Alam, M. et al., "Inhibitory effect of quercetin in the formation of advance glycationend products of human serum albumin: An in vitro and molecularinteraction study," International Journal of Biological Macromolecules 79 (2015) 336-343.
Ashraf, J. et al., "Quercetin as a finer substitute to aminoguanidine in the inhibition of glycation products," International Journal of Biological Macromolecules 79 (2015) 336-343.
Bhuiyan, M. et al. "Quercetin inhibits advanced glycation end product formation via chelating metal ions, trapping methylglyoxal, and trapping reactive oxygen species," Bioscience, Biotechnology, and Biochemistry, 2017, vol. 81, No. 5, 882-890.
Booth, A. et al., "Thiamine Pyrophosphate and Pyridoxamine Inhibit the Formation of Antigenic Advanced Glycation End-Products: Comparison with Aminoguanidine," Biochemical and Biophysical Research Communications 220, 113-119 (1996).
Elosta, A. et al., "Natural Products as Anti-glycation Agents: Possible Therapeutic Potential for Diabetic Complications," Current Diabetes Reviews, 2012, 8, 92-10.
Engelen, L. et al., "Current therapeutic interventions in the glycation pathway:evidence from clinical studies," Diabetes, Obesity and Metabolism 15: 677-689, 2013.
Karachalias, N. et al., "High-Dose Thiamine Therapy Counters Dyslipidemia and Advanced Glycation of Plasma Protein in Streptozotocin-Induced Diabetic Rats," Ann. N.Y. Acad. Sci. 1043: 777-783 (2005).
Kousar, S. et al., "Antiglycation activity of Thiamin-HCl and Benfoitiamine in diabetic condition," J Pak Med Assoc vol. 62, No. 10, Oct. 2012.
Li, X. et al., "Quercetin Inhibits Advanced Glycation End Product Formation by Trapping Methylglyoxal and Glyoxal," Journal of Agricultural and Food Chemistry, 2014, 62, 12152-12158.
Liu, J. et al., "The In Vitro Protective Effects of Curcumin and Demethoxycurcumin in Curcuma longa Extract on Advanced Glycation End Products-Induced Mesangial Cell Apoptosis and Oxidative Stress," Planta Med 2012; 78: 1757-1760.

(Continued)

*Primary Examiner* — David J Blanchard
*Assistant Examiner* — Sarah J Chickos
(74) *Attorney, Agent, or Firm* — Nixon & Vanderhye

(57) ABSTRACT

The present invention relates to a physicochemically stable pharmaceutical composition, in a unit dose characterized in that it comprises effective amounts of 5 the active ingredients thiamine (Vitamin B1), pyridoxine (Vitamin B6), a flavonoid such as quercetin and a polyphenol such as curcumin, or their pharmaceutically acceptable salts in combination with pharmaceutically acceptable excipients, for the prevention of the formation and/or trapping of advanced glycation end products (glyoxal, methylglyoxal, Ni-carboxymethyl-iysine, N-carboxyethyl-lysine, pyrraline, pentosidine, lysine dimer, etc.), which can be used in the treatment and/or prevention of complications of diabetes mellitus (diabetic neuropathy, nephropathy and retinopathy). The pharmaceutical composition of the invention is presented orally, preferably in capsule, pill or sachet for oral administration.

29 Claims, 5 Drawing Sheets

(56) References Cited

OTHER PUBLICATIONS

Nabavi, S. et al., "Curcumin: A Natural Product for Diabetes and its Complications," Current Topics in Medicinal Chemistry, 2015, 15.
Nagai, R. et al., "Inhibition of AGEs formation by natural products," Amino Acids (2014) 46:261-266.
Polizzi, F.C. et al., "Increased DNA-Glycation in Type 2 Diabetic Patients: The Effect of Thiamine and Pyridoxine Therapy," Exp Clin Endocrinol Diabetes 2012; 120: 329-334.
Rabbani, N. and Thornalley, P.J., "Emerging role of thiamine therapy for prevention and treatment of early-stage diabetic nephropathy," Diabetes, Obesity and Metabolism 13: 577-583, 2011.
Sajithlal, G.B. et al., "Effect of Curcumin on the Advanced Glycation and Cross-linking of Collagen in Diabetic Rats," Biochemical Pharmacology, vol. 56, pp. 1607-1614, 1998.
Sun, Y. et al., "Curcumin inhibits advanced glycation end product-induced oxidative stress and inflammatory responses in endothelial cell damage via trapping methylglyoxal," Molecular Medicine Reports 13: 1475-1486, 2016.
Thornalley, P., "The Potential Role of Thiamine (Vitamin B1) in Diabetic Complications," Current Diabetes Reviews, 2005, 1, 287-298.

\* cited by examiner

ADVANCED GLYCATION END PRODUCTS (AGEs)

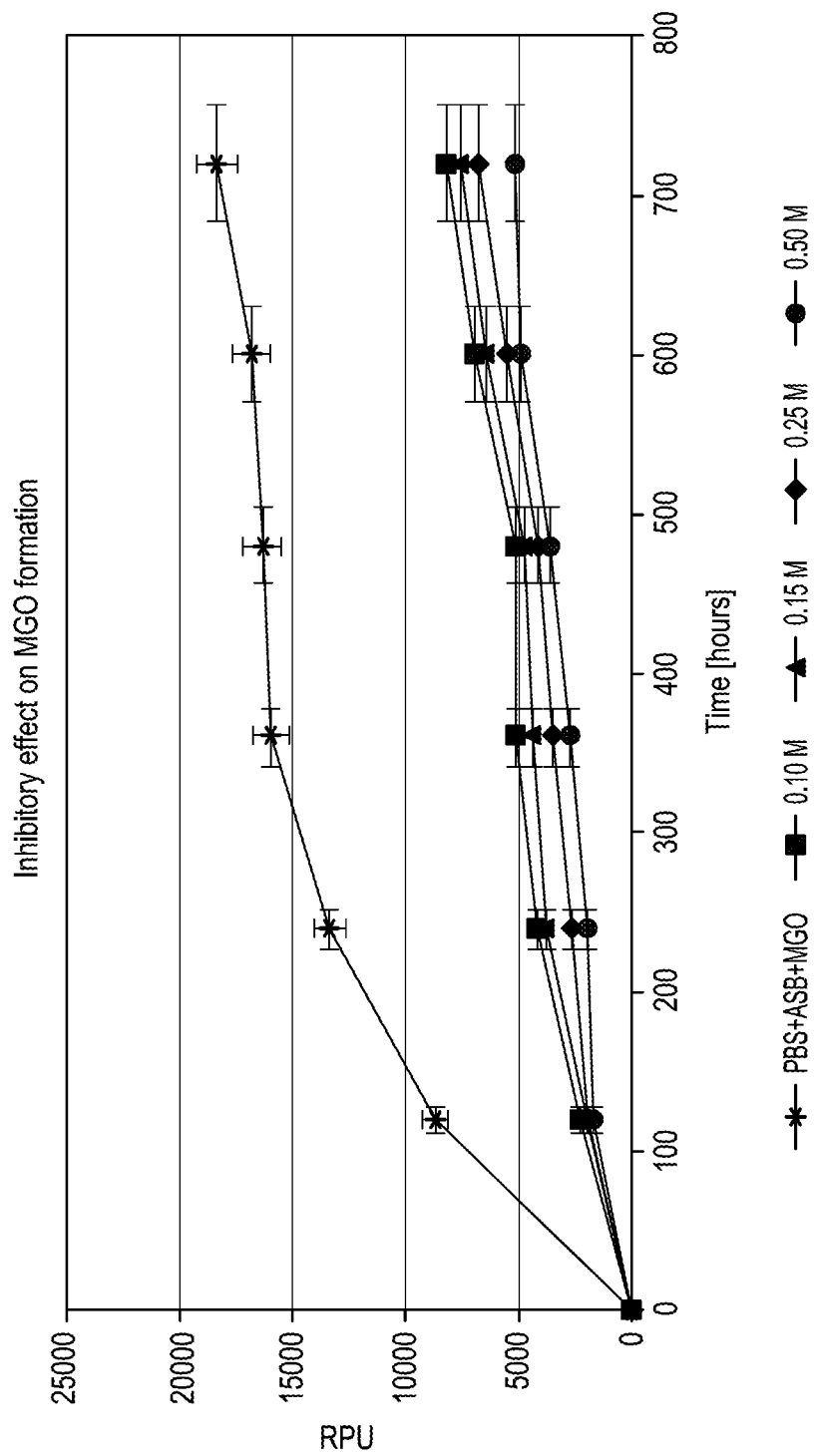

COMBINED PHARMACEUTICAL COMPOSITION

FIELD OF THE INVENTION

The present invention relates to a pharmaceutical composition in capsules, pills or powder comprising the combination of Thiamine (Vitamin B1), Pyridoxine (Vitamin B6), a Flavonoid such as Quercetin and a Polyphenol such as Curcumin and its acceptable pharmaceutical salts, additionally pharmaceutically acceptable carriers, excipients and preservatives; as well as the use of the combination for the preparation of a medicament with complementary therapeutic activity indicated in the prevention of the formation and/or trapping of advanced glycation end products (glyoxal, methylglyoxal, N-carboxymethyl-lysine, N-carboxyethyl-lysine, pyrraline, pentosidine, lysine dimer etc.), and which can be used to prevent the complications of diabetes mellitus (diabetic neuropathy, nephropathy and retinopathy).

BACKGROUND OF THE INVENTION

The Advanced Glycation End Products [AGEs] are a spectrum of heterogeneous compounds which derive from proteins, lipids and nucleic acids which are glycated and oxidized in non-enzymatic form, in a process called Maillard reaction. The Maillard reaction is initiated as a reaction between the carbonyl group of a reducing sugar and an amino group free from a protein, a lipid or a nucleic acid and leads to the formation of an unstable Schiff Base. This reaction is reversible and requires a few hours to occur. Over several weeks these labile compounds give rise to a more stable Amadori product. Subsequently and within months, a part of the Amadori compounds undergo irreversible reactions (oxidation, dehydration and degradation) resulting in AGEs, which are highly stable compounds. It occurs both inside the body, and when preparing food containing sugars, lipids and proteins and which are processed. The formation of in vivo and in vitro AGEs depends on the turnover rate of the chemically modified targets, time and sugar concentration. AGEs alter the structure and function of molecules and increase oxidative stress in biological systems. AGEs are produced normally and accumulate with age. In the normal aging, the formation of AGEs is slower and occurs particularly over long-lived proteins. In diabetes mellitus (DM) the formation and accumulation of AGEs is accelerated due to high blood glucose levels.

From the medical point of view, glycation has been implicated in several pathologies, specifically in DM and neurodegenerative diseases, as well as in the aging process. DM, characterized by hyperglycemia, is associated with irreversible microvascular and macrovascular complications which include diabetic retinopathy, neuropathy, nephropathy. Among several proposed mechanisms, there is evidence indicating that glycation leads to chemical modifications of the proteins that contribute to the pathogenesis of diabetic complications, furthermore an inverse relationship between the strict control of the hyperglycemia and the severity of complications of diabetes has been reported. This relates to the fact that the greatest damage in diabetic patients occurs in collagen-rich tissues and organs and where the entry of glucose is not regulated by insulin, such is the case of the kidney, retina and vascular endothelium, this strongly supports the hypothesis of glycation. Several mechanisms have been proposed, by which glycation leads to diabetic complications. It is known that a heterogeneous group of AGEs is formed by sequential glycation and by glyco-oxidation reactions. Some AGEs such as carboxymethyl-lysine and pentosidine, have become useful markers of glyco-oxidative damage.

The formation of AGEs occurs through a series of chemical reactions; in the first one, the carbonyl group of a ketone or aldehyde of a reducing sugar, binds to a free amino acid (mainly lysine and arginine) of a protein, lipid or DNA, in a non-enzymatic manner to form a Schiff base. The early glycation adducts (Early Glycation Adducts, EGAs), correspond to these initial products (Schiff bases and Amadori products or fructosamines). The reaction mechanisms which lead from EGAs to AGEs, have not been fully studied. The start of these transformations depends on the glucose concentration and takes place in a few hours. if the glucose concentration decreases, the reaction is still reversible. However, if the reaction runs its course, the Schiff base undergoes a chemical rearrangement and forms the called Amadori products or fructosamine, this occurs over a period of days. The Amadori products are more stable than the Schiff bases, but even at this point the reaction is partially reversible. An example of Amadori product is the glycosylated hemoglobin (HbA1c), which is formed by an N-terminal valine residue of a hemoglobin b chain which reacts with glucose and which is usually used as a glycemic control marker. If these reactions continue to develop and the hyperglycemia persists, there will be an accumulation of Amadori products, which will undergo complex chemical rearrangements (oxidations, reductions and hydrations) and form cross-linked proteins. Subsequently, the glyoxal and 3-deoxyglucosone oxidizing dicarbonyls will be formed, which are products of the deglycosylation by the Amadori product, and which are powerful glycation and oxidizing agents, capable of catalyzing new glucose-protein binding reactions. In this stage, several protein glyco-oxidation reactions occur, all of them tending to form glycation products which, since they are bound to a single protein, do not form a bridge between two of them (pyrraline and N-carboxymethyl-lysine). This process is developed over weeks and even months and is irreversible. The final stage in the formation of AGEs, begins with the binding of pyrraline and N-carboxymethyl-lysine with a second protein, forming structures known as DOLD and GOLD bridges, which irreversibly alter the tertiary and quaternary structures of proteins. All these AGEs are very stable to mechanical forces and proteolytic degradation, due to the cross-linked structures which form during glycation and accumulate inside and outside cells and interfere with the function of proteins. Protein glycation is accompanied by an increase in the activity of free radicals. Not only is the appearance of these molecules relevant, but their interaction with their own receptors, which are known as RAGE.

The specific receptors for AGEs can modulate the uptake and removal of AGEs from cells, through the endocytosis and degradation of modified molecules of AGEs. RAGEs are members of the immunoglobulin superfamily-type cell surface molecules, which can recognize a wide range of chemical structures and are expressed in a wide variety of cell types. They consist of an extracellular region containing a V-type immunoglobulin domain and two C-type domains. RAGEs are induced by proinflammatory signals, and their biological activity depends on their binding to a variety of ligands. RAGEs act as a receptor of various ligands released by inflamed, stressed and damaged cells. The increased expression of cell surface RAGE and the accumulation of its ligands, has been observed in a wide range of disorders characterized by chronic inflammation, such as chronic intestinal disease, rheumatoid arthritis, atherosclerosis, Alzheimer's disease and vascular complications of diabetes.

In addition, RAGEs, activate a very wide range of signal transduction cascades: the family of the mitogen-activated proteins kinases (MAP-kinases), members of the signaling family of Janus-kinase signal transducers and activators of transcription (JAK-STAT), cell division control protein 42 (CDC42), ras-related gene to 3 substrate 1 (RAC1) and other members of the Ras family, nuclear receptor coactivator 1 (SRC1 or NCOA1), members of the protein-coding gene signaling family (SMAD) and phosphatidyl-inositol3-kinase.

The main mechanism of degradation of tissues and cells modified by AGEs is through specific receptors for AGEs in macrophages. After degradation, small soluble peptides of AGEs are released and cleansed by the kidneys. A kidney function impairment results in the accumulation of AGEs which can lead to an endothelial disorder and, therefore, to a vascular disease. In diabetic individuals, however, the kidney excretion of AGEs is affected, therefore, they present high plasma levels of AGEs and the urinary excretion of AGEs is reduced. This situation implies that AGEs accumulate in a plasmatic manner and therefore, there is a certain risk of reaction and that new cross-links with plasma proteins are produced. Among the mechanisms through which AGEs produce tissue and organ damage, are the following: modification of extracellular functional proteins and structural proteins, generation of intracellular signaling processes through junctions to membrane receptors and intracellular protein modification.

It is generally accepted that half-lives proteins longer than a few weeks are more susceptible to form advanced glycation end products and consequently that the highest concentrations of AGEs are observed in structural proteins such as those existing in the connective tissue and in the basement membranes. However, it has been seen that AGEs can produce on short half-life proteins, such as plasma proteins, on lipid constituents and nucleic acids. This is particularly important in situations where there is a greater accumulation of AGEs, such as diabetes and kidney disease.

The effects caused by AGEs can be classified as dependent or independent of the receptor: in addition, AGEs can act intracellularly or circulate and interact with the receptors located on the surface of certain cells such as the receptor for AGEs (RAGE). The structural components of the connective tissue matrix and particularly the components of the basement membranes such as type IV collagen, are preferred targets for glycation, but other long half-life proteins, can also be object of advanced glycation, including myelin, tubulin, the plasminogen activator 1 (PAI-1) and fibrinogen. The formation of intra and intermolecular cross-links with collagen as a result of the glycation process, leads to structural alterations which entail a loss of elasticity and an increase in resistance to proteolytic digestion. For example, the cross-linking of collagen type 1 and elastin, leads to a greater rigidity of the blood vessels. The composition of the extracellular matrix is also modified by AGEs, with increased expression of extracellular matrix proteins including fibronectin, collagen type III, IV and V and lamina, possibly induced by overexpression of profibrotic cytokines such as tumor growth factor-$\beta$ (TGF-$\beta$) and connective tissue growth factor (CTGF).

The effects caused by AGEs by the receptor-dependent pathway are triggered by the interaction of AGEs with different receptors capable of joining chemical structures typical of AGEs. The most widely studied receptor is the so-called receptor for AGEs (RAGE), but other receptors identified are the receptors for AGEs 1, 2 and 3 (AGE-R1, AGE-R2 and AGE-R3) the ezrin, radixin and moesin family.

RAGE belongs to the immunoglobulin superfamily and the interaction of AGE with RAGE triggers the activation of second messengers such as protein kinase C and the translocation of the nuclear factor enhancer of the kappa light chains of activated B cells (NF-kB) to the nucleus, where the transcription of proteins increases including ICAM-1, E-selectin, endothelin-1, tissue factor, vascular endothelium growth factor (VEGF) and proinflammatory cytokines.

The promoter region of RAGE contains functional elements para the binding of NF-kB and a consequence is the translocation of NF-kB is the overload of RAGE, thus creating a vicious circle which perpetuates inflammation.

The non-enzymatic glycation of the collagen strands causes a greater cross-linking, due to intermolecular bridges; this makes it less soluble and less susceptible to the enzymatic digestion, giving greater rigidity to the tissue containing it. These cross-links, unlike those produced by the lysyl oxidase enzyme at specific sites of the carboxy- and amino-terminal ends of the collagen, are random and along the collagen molecule.

In the extravascular matrix, collagen glycation sites can act as a network for plasma trapping of albumin, immunoglobulins and low-density lipoproteins (LDL). Trapping in the vascular matrix of LDL depends linearly on the concentration of AGEs which are covalently bound to the collagen. The vascular wall of diabetic patients is characterized by a greater permeability towards plasma proteins in the extracellular matrix, by an early and progressive deposition of plasma proteins in the extracellular vascular matrix and by an accelerated arteriosclerosis.

The peripheral neuropathy of diabetes, is associated with segmental demyelination, axonal degeneration and excessive glycation of the peripheral nerve myelin. In diabetic neuropathy, it has been seen that glycation of tubulin inhibits its polymerization, this mechanism is partly responsible for the axonal transport abnormalities of proteins. In addition to this effect on the axonal transport, glycation is also responsible for the inactivation of Na+-K+-ATPase. It has been proven that this enzyme in the glycated form, is unable to transport K+. Also, it has been observed that certain inhibitors of aldose reductase restore the functionality of the molecule. The presence of specific receptors for proteins modified by glucose has been detected in the macrophages. This shows that glycated myelin is eliminated through these receptors; this process would explain the demyelination of the nerve in diabetic patients.

In patients with diabetes, the risk of mortality from cardiovascular complications is 2 to 4 times higher than in the general population: hyperglycemia is the anomaly that defines DM, and it is logical to assume that high glucose concentration is, at least in part, responsible for the great mortality seen in diabetes. Glycation possibly represents a mechanism by which excessive levels of glucose in plasma and interstitial spaces give rise to the observed pathophysiological changes.

There is a remarkable association between concentrations of glycoxidation products in tissue collagen (adjusted by age), and the degree of diabetic complications, however, the causality between the formation of glycoxidation products and the development of complications has not been established yet. Strong evidence in favor of the fact that AGEs and glycoxidation products would be implicated in the development of diabetic complications is that aminoguanidine, an in vitro inhibitor of advanced glycation reactions, also inhibits a wide range of complications in diabetic animals.

AGEs are recognized by specific cell receptors for AGEs, located in a large variety of cells and collectively referred to as RAGEs, said binding causes a series of cellular responses which include reactive oxygen production, inflammatory response, alteration of gene expression, cytokine secretion, cell proliferation and tissue remodeling.

In tissues, as the age of the organism increases, AGEs accumulate, and this process accelerates in diabetes. Serum levels of AGEs correlate inversely with kidney function and are particularly high in diabetics with kidney disease. Many studies show that reactive AGEs can alter the physical and structural properties of the extracellular matrix, inducing cross-linking between collagen strands, thickening of basement membranes or covalently trapping plasma proteins such as low-density lipoprotein (LDL) and immunoglobulin G (IgG). On the other hand, AGEs participate in a series of cellular responses which result in vascular dysfunction, matrix expansion, arteriosclerosis and glomerulosclerosis.

In diabetes, there is an acceleration of the aging of collagen which, prematurely, gives rise to the first symptoms, such as cataracts, osteoporosis, osteoarthritis, the weakening of the immune system, and in general, the rigidity of the tissues. All the effects cannot be attributed solely to the Maillard reaction, however, to a large extent, its modulation depends on the average long-term blood glucose. The quantification of pentosidine in rat tendons reveals that dietary restriction is accompanied by decreased synthesis of pentosidine, suggesting a profound effect of carbohydrates catalyzing the reaction. In the lens of diabetic patients, glycation causes protein cross-linking and, therefore, the formation of aggregates; on the other hand, these become more susceptible to oxidation due to the alteration of their structure, all this facilitates the appearance of cataracts.

The glycation process of proteins, sugars and lipids has been associated with mechanisms of development of various diseases and complications, such as retinopathy, neuropathy and nephropathy associated with diabetes mellitus, macrovascular disease, Alzheimer's disease, and aging. Complications of diabetes are directly related to the role that hyperglycemia plays in it, which can be investigated by the relationships between glycemic control and these complications. Damages produced by hyperglycemia involve complex interactions between individual's genetics, smoking, body mass index, dyslipidemia, alterations of coagulation factors. Intracellular mechanisms involved in these complications include: increase in the flow of the polyols pathway, activation of protein kinase C, increase in the hexosamines pathway, and increase in the formation of AGEs. The damage produced by these mechanisms is related to oxidative stress. Many of the effects of hyperglycemia in diabetes are mediated by AGEs, which lead to the formation of reactive and unstable intermediates that rapidly form intra- and intermolecular covalent cross-links or glyco-oxidation products.

Diabetic retinopathy has become a vascular complication which is more strongly associated with diabetes and the main cause of blindness among adults aged 20 to 74 years. The poor control of blood glucose and blood pressure complicates this disease. Multiple pathways have been associated with the pathogenesis of diabetic retinopathy, including the polyol pathway, the activation of diacylglycerol and the protein kinase C pathway; nevertheless, the AGE interaction and its receptor (RAGE) has been studied more recently. Clinically, this disease is classified into non-proliferative and proliferative diabetic retinopathy. The first one is characterized by capillary microangiopathy, microaneurysms, thickening of the basement membrane and loss of pericytes. Many of these events are a consequence of the endothelial dysfunction produced by the AGE-RAGE interaction. In proliferative diabetic retinopathy, the activation of RAGE in Müller's glia results in the activation of extracellular signal-regulated kinases (EKR½) and the subsequent production of inflammatory cytokines, such as vascular endothelial growth factor (VEGF) and metalloproteinase 1 (MCP-1), which implies a critical role of RAGE in neovascularization and the selection of immune cells in the layers of the retina. Other consequences of the deleterious effects of RAGE in diabetic retinopathy include rupture of the blood-retinal barrier and increased leukotaxis. Diabetic nephropathy, characterized by the development of proteinuria and a decrease in the glomerular filtration rate, represents the main cause of end-stage kidney disease worldwide. One aspect of great importance is the accumulation of AGEs which occurs at the kidney level in diabetic patients. In this organ, RAGE is expressed in podocytes and endothelial cells. One of the effects produced by AGEs at the kidney level is the hypofunction of glyoxalase 1, a cytosolic enzyme responsible for detoxifying methylglyoxal. Therefore, the kidney contributes to higher levels of AGEs in the plasma. Studies in transgenic mice overexpressing RAGE, showed significant increases in kidney weight, albuminuria and glomerulosclerosis, once again demonstrating the importance of RAGE.

Diabetic neuropathy is characterized by an alteration in sensitivity to vibrations, thermal thresholds and pain. The endothelial injuries caused by AGEs can affect blood flow, lead to a state of hypoxia, oxidative stress and, finally, to the deterioration of the nerve fiber. The AGE-RAGE interaction and the progression of this disease has been demonstrated by the identification of RAGE, both in endoneurial and perineural vessels. In addition, some studies in experimental models have shown that the HMGB1 protein coding gene, a RAGE ligand, contributes to neuropathic pain after a nerve injury, and the interruption of HMGB1/RAGE signaling could be a promising therapeutic strategy.

Histopathological studies have shown that, apart from diabetes, AGEs accumulate in a wide variety of tissue types and associate mainly with conditions of chronic inflammation, including coronary atheroma, renal cortex, mesangial and glomerular basement membrane, amyloid plaques in Alzheimer's disease, in cartilage of rheumatoid arthritis, cardiac muscle, lung and liver and osteoarthritis.

On the other hand, it is demonstrated that the concentrations of AGEs increase in those patients who became diabetic and that such increase is systemic in the following organs and tissues: kidneys, piles and vascular tissue. Studies in patients have shown that the concentration of Carboxymethyl-lysine (CML), methylglyoxal, glyoxal, among other AGEs, increase significantly in those patients who have complications associated with diabetes, such as nephropathy, retinopathy, neuropathy and atherosclerosis. On the other hand, autoxidation of glucose is linked to the generation of reactive oxygen species (ROS), such as superoxide radicals. ROS, in turn, increase glycation and both mechanisms interfere with a wide variety of physiological processes promoters of atherogenesis.

Several studies have shown that pharmacological intervention is capable of interfering with AGEs (directly or indirectly) producing beneficial effects in diabetic complications. Therapeutic interventions to reduce AGEs should be directed towards the reduction of the formation of AGEs and crossed-links or the trapping of the AGEs already formed. Aminiguanidine, is perhaps the best known and experimentally, most widely used inhibitor of formation of AGEs. Unfortunately, its application to the clinic is limited due to its severe adverse events, such as the induction of autoantibody formation, rapidly progressive glomerulonephritis and anemia. Other promising agents are benfotiamine and pioglitazone.

It is clearly demonstrated that reductions in AGEs (glyoxal, methylglyoxal, N-carboxymethyl-lysine, N-carboxyethyl-lysine, etc.) decrease the complications of diabetes mellitus. Hence, the urgent need to have safe and effective formulations that include active ingredients to prevent the complications of diabetes and, if possible, to reverse the complications in a single unit dose, to be administered once a day.

The present invention aims to present a pharmaceutical form in the same unit dose which includes a pharmaceutical composition that prevents the complications of diabetes mellitus and in some cases, reverses the damage produced by AGEs.

The selected drugs are vitamin B1 (Thiamine), vitamin B6 (Pyridoxine) which are powerful blockers of the formation of AGEs, in addition a flavonoid such as quercetin which is a methylglyoxal and glyoxal catcher, as well as a polyphenol such as curcumin which has an effect on the formation of adducts and a chelating effect with AGEs.

Using combined Thiamine, Pyridoxine, Quercetin and Curcumin, results in a synergistic pharmacological action, indicated in the prevention of complications caused by the advanced glycation end products as is the case of diabetes mellitus. From the pharmacodynamic point of view, the combination of Thiamine, Pyridoxine, Quercetin and Curcumin is quite rational, since they induce a synergistic effect as inhibitors of AGEs, with different mechanism of action and have a favorable effect for the prevention of complications of diabetes mellitus, in addition to its safety profile.

The combination of thiamine, pyridoxine, quercetin and curcumin has a therapeutic activity superior to that expected in mono-pharmaceutical therapies, due to the synergistic effect of the four active ingredients.

The resulting formulation of the present invention offers a stable, safe and effective medicament, due to its inhibitory effect on the reduction of AGEs (glyoxal, methylglyoxal, N-carboxymethyl-lysine, N-carboxyethyl-lysine, pyrraline, pentosidine, methylglyoxal-lysine dimer, glyoxal-lysine dimer, etc.), which is indicated for the prevention of diabetic complications such as neuropathy, retinopathy, cardiomyopathy and nephropathy and their related morbidities, such as diabetic foot, blindness, heart failure and kidney failure, which can be administered once a day.

SUMMARY OF THE INVENTION

The present invention relates to an oral, physicochemically stable pharmaceutical composition, in a unit dose characterized in that it comprises effective amounts of the active ingredients thiamine (Vitamin B1), pyridoxine (Vitamin B6), a flavonoid such as quercetin and a polyphenol as the curcumin, or its pharmaceutically acceptable salts in combination with pharmaceutically acceptable excipients, for the prevention of the formation of advanced glycation end products (glyoxal, methylglyoxal, N-carboxymethyl-lysine, N-carboxyethyl-lysine, pyrraline, pentosidine, lysine dimer, etc.), which can be used in the treatment and/or prevention of complications of diabetes mellitus (diabetic neuropathy, nephropathy or retinopathy).

The pharmaceutical composition of the invention is presented orally, preferably in capsule, pill or sachet for oral administration.

BRIEF DESCRIPTION OF THE DRAWINGS

FIG. 5. Inhibitory effect of methylglyoxal formation by the combination of thiamine, pyridoxine, quercetin and curcumin in 4 concentrations (0.10, 0.15, 0.25 and 0.50 M), in an in vitro system with bovine serum albumin and methylglyoxal for 120, 240, 360, 480, 600 and 720 hours.

DETAILED DESCRIPTION OF THE PREFERRED EMBODIMENTS

Figure 1:
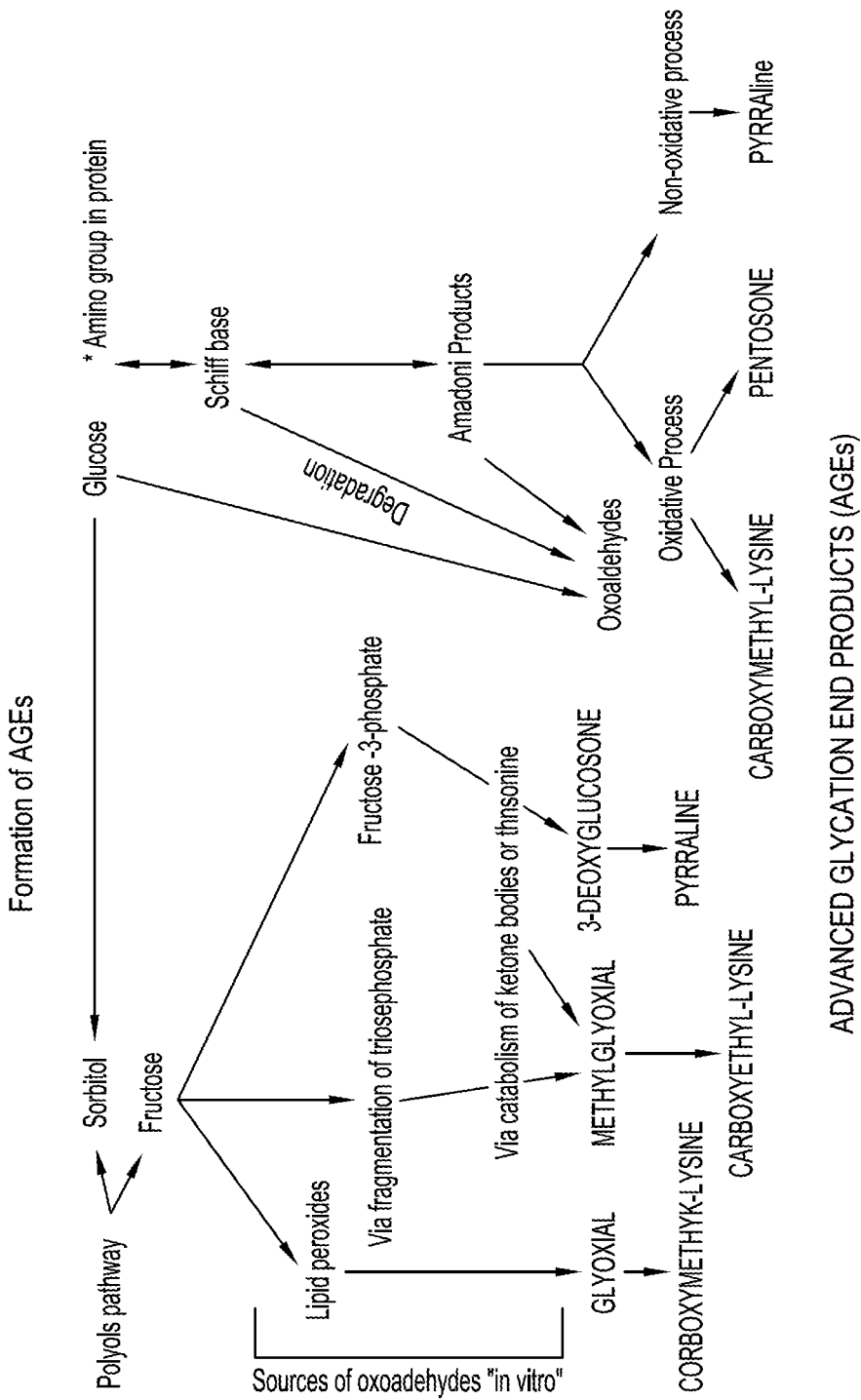
FIG. 1. Generation process of AGEs in which the polyols route and the formation of oxo-aldehydes are incorporated.

The present invention provides a pharmaceutical composition useful for the prevention of the formation of advanced glycation end products (glyoxal, methylglyoxal, N-carboxymethyl-lysine, N-carboxyethyl-lysine, pyrraline, pentosidine, methylglyoxal-lysine dimer, glyoxal-lysine dimer, etc.), which can be used in the treatment and/or prevention of complications of diabetes mellitus (diabetic retinopathy, neuropathy and nephropathy) and its comorbidity related to a single unit dose, to be administered once a day.

The present invention provides a pharmaceutical composition comprising Vitamin B1 selected from thiamine, thiamine diphosphate, thiamine triphosphate or its pharmaceutically acceptable salts, Vitamin B6 selected from pyridoxine, pyrodoxamine, pyritinol, pyrithioxin, dipyridoxolyldisulfide, pyridoxindisulfide or its pharmaceutically acceptable salts, a flavonoid selected from quercetin, quercetin-3-4'-glucoside, quercetin-3-galactoside, quercetin-3-glucoside, quercetin-3-rhamnoside, quercetin-3-rhamnoglucoside, quercetin-3-arabinoside or its pharmaceutically accepted salts and a polyphenol selected from curcumin, demethoxycurcumin, bisdemethoxycurcumin or its pharmaceutically accepted salts in a single dose, to be administered once or twice a day.

Advanced glycation is one of the major pathways involved in the development and progression of different diabetic complications including, nephropathy, retinopathy, and neuropathy. There is evidence from animal studies that exposure to high exogenous levels of AGEs contributes to kidney and vascular complications.

The effects of AGEs can be prevented if end products of glycation are blocked or trapped; however, the development of specific inhibitors for the formation of AGEs has been made impossible due to the complexity of the reactions involved in their formation and the diversity of products formed. Aminoguanidine, was one of the first studied inhibitors of AGEs and it is believed that it acts trapping the intermediary carbonyl compounds of metabolism, however, due to adverse events, it has not been used in therapeutics. Research in the pharmaceutical industry focuses on the development of analogues of aminoguanidine and other class of compounds, such as natural nutraceuticals, capable of inhibiting the non-enzymatic reactions of the Maillard reaction.

It is known that preventive medicine is the most important scope to prevent the development of diseases related to lifestyle, such as atherosclerosis and diabetic complications. The daily intake of AGE inhibitors in natural products can play a beneficial role in the prevention of the pathogenesis of diseases related to quality of life. However, the doses of these inhibitors of AGEs in the daily diet do not provide the necessary concentrations sufficient for these compounds to significantly inhibit the formation of AGEs, which causes the need to obtain them in preparations specifically designed for therapeutic doses. It is believed that the daily intake of inhibitors of AGEs in natural products can play a beneficial role in the prevention of the pathogenesis of lifestyle-related diseases. Therefore, natural compounds are presented as an alternative of potential inhibitors of the formation or trapping of AGEs. Bovine serum was incubated with ribose in the presence or absence of natural compounds in sodium phosphate buffer and the level of CML formation was determined. Consequently, several natural compounds such as glycyrrhizin, glycylrhetinic acid and quercetin, significantly inhibited the formation of CML, while other compounds, including epicatechin, acteoside and gallic acid, increase the formation of CML.

Glycoxidation is a term used for the glycation process involving oxidation. The non-enzymatic glycation of proteins by glucose leads to the formation of toxic and immunogenic AGEs. Among the inhibitors of this biochemical event, both thiamine and pyridoxine have proven to inhibit the formation of AGEs and have shown greater effectiveness than aminoguanidine. This suggests that these two compounds may have a novel therapeutic potential in preventing vascular complications of diabetes. Although aminoguanidine inhibits the initial stages of glycation in patients with hyperglycemia, this agent minimally inhibits the formation of post-Amadori AGEs. Thiamine corrects delayed replication and decreases the production of lactate and AGEs in venous endothelium under conditions of high glucose concentrations.

Non-enzymatic glycation of proteins by glucose leads to the formation of toxins and AGEs, which may be the major contributors to pathological manifestations of diabetes mellitus, aging and possibly neurodegenerative diseases. In in vitro studies, the inhibitory effect of the formation of AGEs on bovine serum albumin, ribonuclease A and human hemoglobin was evaluated by several derivatives of vitamin B1 and B6. Among the inhibitors pyridoxamine, pyridoxine and thiamine, potentially inhibited the formation of AGEs and were more effective than aminoguanidine, suggesting that these three compounds have a therapeutic potential in the prevention of vascular complications of diabetes.

It is well known that advanced glycation plays an important role in the progression of diabetic complications. Although several studies have been conducted on protein glycation, studies related to DNA glycation are limited. One study focused exclusively on investigating the glycation of DNA in diabetes mellitus and secondarily on evaluating the effects of thiamine and pyridoxine. The study involved two groups of diabetic patients, with and without nephropathy. Both groups of patients received thiamine and pyridoxine for 5 months. DNA glycation was determined in leukocytes. The levels of glycated DNA were significantly higher in patients with nephropathy at the beginning of the study, but after 5 months of treatment with thiamine and pyridoxine, there was a significant decrease in glycated DNA. The study showed that the combined administration of thiamine and pyridoxine in patients with diabetic nephropathy causes a decrease in the glycated DNA in leukocytes.

The accumulation of triose phosphates is increased by the high concentrations of cytosolic glucose in hyperglycemia and is a potential trigger for biochemical dysfunction that leads to the development of diabetic complications. This can be prevented by eliminating the excess of triose phosphates, through the reductive pathway of pentose phosphates. This pathway is altered in clinical and experimental diabetes due to thiamine deficiency. The expression and activity of the thiamine-dependent enzyme, transketolase, the facilitating enzyme of the reductive pathway of pentose phosphate, is consequently reduced. The correction of thiamine deficiency in experimental diabetes with high-dose thiamine therapy restores the disposition of triose phosphates by the pentose phosphate reductive pathway in hyperglycemia. This multiple mechanism prevents biochemical dysfunction: activation of protein kinase C, activation of the hexosamine pathway, increased glycation and oxidative stress. Consequently, the development of incipient diabetic nephropathy, neuropathy and nephropathy are prevented. High doses of thiamin, also correct dyslipidemia in experimental diabetes, normalizing cholesterol and triglycerides.

In experimental streptozotocin-induced diabetic rat models it has been found a significant increase in the levels of glyoxal (115%) and methylglyoxal (68%) with respect to normal values and these were normalized with thiamine and benfotiamine, while the values of N-carboxymethyl-lysine (CML) and N-carboxyethyl-lysine (CEL) were increased by 74% and 118%, respectively in this type of diabetic rats. Values of CML and CEL were normalized only with thiamine. A recent study evaluated the peptide levels of circulating AGEs in patients with diabetic nephropathy when treated with thiamine and pyridoxine. At the end of the 5 months of study it was found that the group of patients who did not receive the treatment showed an increase in the circulating levels of AGEs, while the patients who received thiamine plus pyridoxine, showed a significant decrease not only of AGEs but also of HbA1c and an increase in C-peptide.

Thiamine supplementation can prevent and reverse diabetic nephropathy in its initial state. This probably occurs due to the fact of maintaining the activity and expression of thiamine pyrophosphate-dependent enzymes, which helps to counter the adverse events of high glucose concentrations, particularly transketolase. Evidence from experimental and clinical studies suggests that metabolism and clearance of thiamine is altered in diabetes, leading to a tissue-specific thiamine deficiency in the kidney and other sites developing vascular complications. Thiamine supplementation prevents the development of early stage nephropathy in diabetic rats and recent clinical studies have shown that increased urinary albumin excretion is reversed by thiamine in patients with type 2 diabetes and microalbuminuria. The monophosphate prodrug, benfotiamine, has not shown a protective effect in experimental nephropathy.

Curcumin is the bioactive constituent of the *Curcuma Longa* plant, which has a wide range of physiological and pharmacological properties, such as antioxidant, anti-inflammatory, antineoplastic, neuroprotective and antidiabetic. Antidiabetic activity of curcumin may be due to its potent ability to suppress oxidative stress and inflammation. In addition, it shows a beneficial role in endothelial dysfunction induced by diabetes and induces a deregulation on nuclear factor kappa. Curcumin has a protective effect against advanced glycation as well as on collagen cross-links and through this pathway, mitigates the advanced glycation end products, which induce the complications of diabetes. Curcumin also reduces blood glucose and HbA1c levels in diabetic rats through regulation of the polyol pathway. A close association has been postulated between the increase of oxidative stress and hyperglycemia, which contributes significantly to the accelerated accumulation of AGEs and collagen cross-links in diabetes mellitus. The influence of curcumin, as an efficient antioxidant, on the levels of AGEs and collagen cross-links in diabetic rats has been reported. In one study, diabetic rats received turmeric (200 mg/kg weight) orally for 8 weeks. The antioxidant activity in serum and the levels of AGEs and collagen cross-links were evaluated in tendons of the tail and skin. The oxidative stress observed in diabetic rats was significantly reduced by curcumin. Similarly, the accumulation of lipid peroxidation products in serums was significantly reduced by curcumin. The accelerated accumulation of AGEs in the collagen of diabetic rats, detected by ELISA, was prevented by curcumin. Likewise, the extensive collagen cross-linking in the tendon of the tail and skin was extensively prevented by curcumin. A correlation between the levels of AGEs and collagen cross-links was observed, which suggests a relationship between advanced glycation and cross-links. It was also observed that the preventive effects of curcumin on advanced glycation and collagen cross-links were more pronounced than their therapeutic effect. Methylglyoxal induces oxidative stress and proinflammatory responses, which contribute to endothelial dysfunction. Curcumin can protect endothelial cells against stress-induced damage by trapping dicarbonyl compounds such as methylglyoxal. It has been proven that curcumin significantly inhibits the formation of AGEs, in addition to significantly reducing the expression levels of transforming growth factor-β1 and intracellular adhesion molecule-1. On the other hand, it is known that the formation and accumulation of AGEs contributes to endothelial dysfunction. The trapping of dicarbonyl compounds such as methylglyoxal inhibits the formation of AGEs by attenuating the stress induced by carbonyls in cell damage. Several studies have indicated that curcumin can prevent endothelial dysfunction induced by methylglyoxal by trapping methylglyoxal directly, to form curcumin-methylglyoxal adducts. Based on the above data, evidence that curcumin attenuates the cytotoxicity of dicarbonyl compounds such as methylglyoxal in endothelial damage through methylglyoxal trapping is provided.

Quercetin, a common flavonoid, has proven to be an effective antioxidant in several in vitro systems, including the trapping of oxygenated radicals. The antioxidant activity is attributed to the presence of hydroxyphenolic groups in the flavonoid structure. Currently they have really attracted attention, due to their diverse potentials in human health, for the treatment of diabetes, allergy, asthma, cardiovascular diseases and inflammation. Especially, the effectiveness of quercetin for inhibiting the formation of AGEs has increased the interest of several researchers. Flavonoids can trap reactive dicarbonyl species such as methylglyoxal and glyoxal. Methylglyoxal and glyoxal are not only endogenous metabolites, but they also come from exogenous sources such as foods, beverages, the urban atmosphere and cigarette smoke. These reactive dicarbonyls have been identified as precursors of AGEs, which have been associated with the long-term complications of diabetes. The non-enzymatic glycation causes the reaction between the carbonyl group of a sugar with the amino group of a protein, giving rise to a Schiff base and to Amadori products. The formation of AGEs leads to the generation of free radicals, which play an important role in the pathophysiology of diabetes. The bioavailability of antioxidants in the diet, such as quercetin, inhibit the formation of AGEs. Numerous compounds have been investigated for their antiglycation activity. These compounds can act by (i) blocking the free-protein amino group, preventing glycation by free sugars or (ii) blocking the carbonyl groups from the reduced sugars, therefore, reducing the formation of Amadori products and dicarbonyl intermediates, effectively reducing the glycation and/or formation of AGEs. Based on the above, several studies suggest that the effect of quercetin is due to the fact that it binds to the lysine residues 31 and 59 of human albumin which are under glycation and which play a decisive role in the formation of AGEs. In addition, it has been reported that the formation of Schiff bases occurs between the free amino group and the carboxyl group of sugar, and since the free amino group is available in lysine, quercetin binds to this lysine. This is a mechanism by which quercetin induces the formation of methylglyoxal-adducts and glyoxal-adducts, thus directly inhibiting the formation of AGEs. Under physiological conditions, quercetin traps up to 50% and 80% of glyoxal and methylglyoxal, respectively, via dose-dependent, forming adducts. On the other hand, physiological concentrations of magnesium, copper and zinc, accelerate the formation of AGEs, only under conditions mediated by glucose and these concentrations are inhibited by direct quercetin chelation. In this way, quercetin inhibits the formation of AGEs. Quercetin inhibits the formation of AGEs mediated by methylglyoxal as well as the formation of AGEs mediated by glucose and ribose. Quercetin quickly traps methylglyoxal and glyoxal and subsequently inhibits the formation of AGEs, through the formation of mono and di-adducts under physiological conditions. It is concluded that the inhibition of the formation of AGEs by quercetin includes the chelating effect, trapping of precursors of AGEs, as well as trapping of reactive oxygen species, which lead to an oxidative degradation.

In addition to its effect on AGEs, thiamine, pyridoxine, quercetin and curcumin, have proven to be safe and effective regarding the following pharmacological indications. Therapeutically thiamine is indicated in metabolic disorders, as a supplement in patients with thiamine deficiency and Wernicke-Korsakoff syndrome among other pathologies at doses from 300 to 1,000 mg per day divided into several doses, either orally or intramuscularly. On the other hand, pyridoxine, which is indicated for the management of anemia, tardive dyskinesia and pyridoxine-dependent seizures; it is administered orally, intramuscularly or intravenously at doses of up to 600 mg per day. Quercetin, a potent antioxidant and peripheral vasodilator, is indicated at doses from 600 to 1,200 mg per day orally. Finally, curcumin with antioxidant, antiviral and antibacterial properties, among others, is administered orally at doses from 500 to 2,000 mg per day.

Formulations

The following describes the formulation in capsules, pills or oral powder containing the active ingredients or pharmaceutically acceptable salts thereof and pharmaceutically acceptable excipients as described below.

Active ingredients comprising:

Thiamine, pyridoxine, quercetin and curcumin or pharmacologically acceptable salts thereof, of the family.

Excipient or pharmacologically acceptable carriers which may include, among others: sodium starch glycolate, microcrystalline cellulose, titanium dioxide, magnesium stearate, methylcellulose, hydroxypropyl cellulose, polyethylene glycol, polyvidone, calcium phosphate, magnesium gluconate, lactose, maltodextrin, avicel.

Pharmacologically acceptable preservatives which may include, among others: benzoic acid, salicylic acid, cresol, ethyl parahydroxybenzoate.

Formulations:
Thiamine 150 mg
Pyridoxine 100 mg
Quercetin 200 mg
Curcumin 200 mg
Excipient q.s.p 1 pill, capsule or sachet
Preservative q.s.p 1 pill, capsule or sachet Compositions of the present invention contain therapeutically effective amounts of thiamine (Vitamin B1) pyridoxine (vitamin B6), quercetin and curcumin and its analogues.

According to the preferred embodiment, the amount of thiamine used can be from 10 mg to 2,000 mg, the amount of pyridoxine is from 10 mg to 2,000 mg, with respect to quercetin, the amount used can be from 10 mg to 2000 mg and finally for curcumin the amounts goes from 10 mg to 2,000 mg.

When thiamine, pyridoxine, quercetin and turmeric are incorporated in the same unit dose, it preferably comprises from 10 mg to 2,000 mg of thiamine, from 10 mg to 2,000 mg of pyridoxine, from 10 mg to 2,000 mg of quercetin and from 10 mg to 2,000 mg of curcumin.

The resulting formulation of the present invention makes it possible to offer a medicament with a complementary, stable, safe and effective effect indicated in the prevention of complications of diabetes mellitus such as diabetic retinopathy, neuropathy, and nephropathy and their related morbidities of immediate release which can be administered once, twice or three times a day.

The invention has been sufficiently described so that a person with average skill in the art can reproduce and obtain the results that we mentioned in the present description. However, any person skilled in the art of the present invention may be able to make modifications not described in the present application. However, if for the application of these modifications in a specific composition the matter claimed in the following claims is required, said compositions should be included within the scope of the present invention.

In Vitro Effect on the Trapping or Inhibition of Advanced Glycation End Products (Glyoxal and Methylglyoxal) by the Combination of Thiamine, Pyridoxine, Quercetin and Curcumin.

INTRODUCTION

Glycation is a non-enzymatic reaction of reduction of free sugars with free-protein amino groups, deoxyribonucleic acid (DNA) and lipids. The reaction begins with the formation of the highly unstable Schiff base, which are transformed into early glycation products, also known as Amadori products. These intermediates, undergo a series of complex reactions, and generate cross-link and fluorescent derivatives, known as advanced glycation end products (AGEs). The accumulation of AGEs in the tissues of the vascular wall and on plasma lipoproteins and the binding to specific receptors for advanced glycation end products (RAGEs) are accelerators of diabetic alterations and play an important role in the development of the complications of diabetes. It is well established that methylglyoxal (MG) forms AGEs by interacting with biomacromolecules, such as DNA, proteins and lipoprotein. Several studies with human subjects have shown that precursors for AGEs derived from the diet, such as N-carboxymethyl-lysine (CML) and MG increase inflammatory responses and oxidative stress in individuals affected with debilitating diseases, such as diabetes mellitus. Thus, CML and MG are intermediates of glycation and precursors for AGEs and are relevant targets for compounds that aim to reduce the undesirable consequences of glycation of proteins both in vitro and in vivo, as it is the case of the complications of diabetes, retinopathy, neuropathy and nephropathy.

There is considerable evidence implicating the formation and accumulation of AGEs as the major factor in the development of complications of diabetes and atherosclerosis. Damaged tissue, particularly in vascular endothelial cells, can originate by activation of key cell signaling systems and stimulate inappropriate cell activities through the secretion of cytokines and vascular cell adhesion molecules. Thus, therapeutic intervention should be aimed at preventing the formation of AGEs and the formation of AGEs-proteins cross-links.

The effect of thiamine on the formation of AGEs has been evaluated and it has proven to be a potent inhibitor of glycation. It has been demonstrated that the levels of glyoxal and methylglyoxal, are increased by 115% and 68% in diabetic rats treated with streptozotocin, with respect to normal controls and these were normalized by thiamine and benfotiamine, while the levels of N-carboxymethyl-lysine and N-carboxyethyl-lysine were increased by 74% and 118% in these diabetic rats and the values were normalized only by thiamine (Ann NY Acad Sci 2005; 1043: 777-783). On the other hand, DNA-glycated levels are significantly elevated in diabetic patients when compared with healthy patients. The combination of thiamine plus pyridoxine induces a significant decrease in the DNA-glycated values, from 564.53% in diabetic patients at the beginning of the study against 254.56% in patients treated with thiamine and pyridoxine (Exp Clin Endocrinol Diabetes 2012; 120 [6]: 329-334). Quercetin, a natural flavonoid found in fruits, vegetables and grains, can effectively inhibit the formation of AGEs in a dose-dependent manner, via the trapping of reactive dicarbonyl compounds. It has been shown in several studies that quercetin traps up to 30% and 50% of glyoxal and methylglyoxal, respectively, within the first hour under physiological conditions. Under these conditions, quercetin forms adducts with both glyoxal and methylglyoxal, which will subsequently be eliminated without causing any damage (Int J Biol Macromol 2015; 79: 336-343). On the other hand, turmeric protects endothelial cells against carbonyl-induced stress damage by trapping dicarbonyl compounds such as methylglyoxal. Thus, the adducts of turmeric-methylglyoxal favor mitigation of endothelial damage. Turmeric traps methylglyoxal in a 1:1 range to form adducts within the first 720 minutes (Mol Med Reports 2016; 13: 1475-1486).

With the previous data, it is assumed that with significant reductions in the levels of AGEs (glyoxal, methylglyoxal, N-carboxymethyl-lysine, N-carboxyethyl-lysine) at the plasma level it is possible to reduce the complications of diabetes mellitus. Hence, the urgent need to have a stable and safe formulation which includes drugs to prevent the complications of diabetes in a single unit dose, to be administered once a day.

The objective of the present study was to evaluate the reduction of the formation of advanced glycation products, Glyoxal and Methylglyoxal through the combination of thiamine, pyridoxine, quercetin and turmeric.

Material and Method

Thiamine, pyridoxine, quercetin and curcumin were obtained from Future Foods S.A. de C.V. (Mexico City), glyoxal (GO, 40% water soluble), methylglyoxal (MGO, 40% water soluble), 1,2-diaminobenzene (DB) and 2,3-butanedione were obtained from Sigma-Aldrich (Mexico City). Human serum albumin (HSA), DMSO, streptomycin and penicillin were donated by the School of Chemistry of UNAM. HPLC grade solvents and other reagents were obtained from the School of Chemistry of UNAM.

GO (0.5 mM) and MGO (0.5 mM) were incubated with thiamine (0.10, 0.15, 0.25 and 0.5 mM), pyridoxine (0.10, 0.15, 0.25 and 0.5 mM), quercetin (0.25, 0.5, 1.5 and 2.5 mM) and curcumin (0.25, 0.5, 1.5 and 2.5 mM) in a PBS buffer (pH 7.4, 100 mM) at 37° C. for 0, 10, 30, 60, 120 or 240 min. At each time, the reaction was stopped to add 10 mcl of acetic acid. Subsequently, the samples were stored at −80° C. to be analyzed later.

One milliliter of 100 mm DB was added to 1 ml of the sample and then mixed with 0.5 ml of 2,3-butanedione (internal standard) at 1 mM. The mixture was maintained at 60° C. for 15 min. Subsequently, 1 ml of 1 M acetaldehyde was added and incubated at 60° C. for 15 min to remove DB that did not react. The mixture was extracted twice with 2 ml of methylene hydrochloride. The organic stage was combined and concentrated to 0.5 ml. One microliter of this sample was injected directly into the gas chromatography (GC). The remaining percentage of GO and MGO was calculated using the following equation:

Remaining %=amount of GO/MGO in the compound test (such as quinoxalines)/amount of GO/MGO in control (such as quinoxalines)×100

The levels of methylquinoxaline and quinoxaline were analyzed with an Agilent gas chromatography (Agilent Technologies, Palo Alto, Calif.) equipped with a flame ionization detector. The column was an HP-S MS (5%-phenyl)-methylpolysiloxane silica capillary (30 m×0.32 mm, film thickness=0.25 μm). The temperature of the injector was 250° C. and the temperature of the detector was 280° C. of hydrogen, air and nitrogen, flow rate of 30.0, 300 and 5.0 ml/min, respectively. The injector was in split mode 1:1. The flow rate of the gas transporter (nitrogen) was 2.0 ml/min. The oven temperature of the GC was programmed as follows: the initial temperature of the oven was 40° C. for the first minute, it was increased to 140° C. at a rate of 5° C./min and kept for 1 min, subsequently it was increased to 250° C. at a rate of 50° C./min and maintained for 1 min. The total time was 25.2 min. All solvents were filtered with a nylaflo membrane filter. The injection volume was 1 μl for each sample of solution.

ASB (1.5 mg/ml) was incubated with GO (500 μl) or MGO (500 μl) in PBS buffer, pH 7.4, in the presence or absence of the combination (thiamine, pyridoxine, quercetin, turmeric) 0.25, 0.25, 1 and 1 mM at 37° C. Streptomycin and penicillin were added (0.3 ml) to the solution to prevent bacterial growth. The reaction mixture (500 μl) was collected and frozen at designated times (0, 4, 8, 12, 72, 144, 288, 432 and 720 hrs). The amount of AGEs was determined using fluorescence at an excitation/wavelength emission of 370/440 nm.

Results

Figure 2:
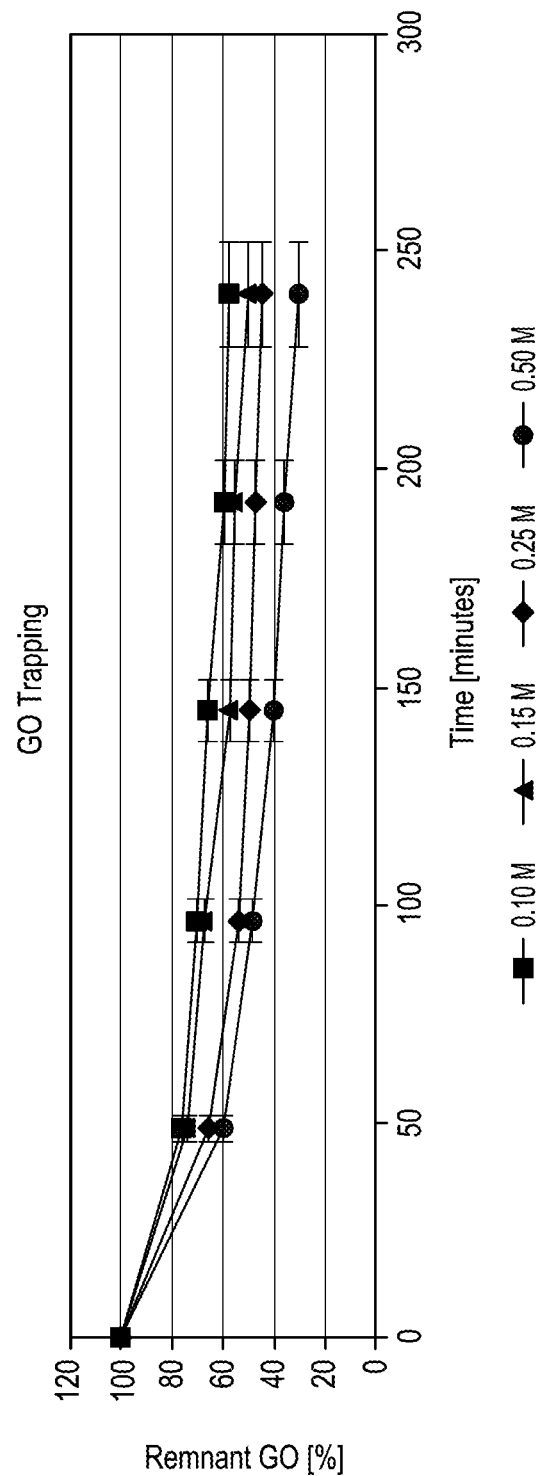
FIG. 2. Glyoxal trapping by different concentrations (0.10, 0.15, 0.25 and 0.50 M) of the combination of thiamine, pyridoxine, quercetin and curcumin under physiological conditions (pH 7.4 and temperature 37° C.). 0.5 M of glyoxal were incubated with the combination of thiamine, pyridoxine, quercetin and curcumin in a phosphate buffer solution at pH 7.4 for 48, 96, 144, 192 and 240 min.
Figure 3:
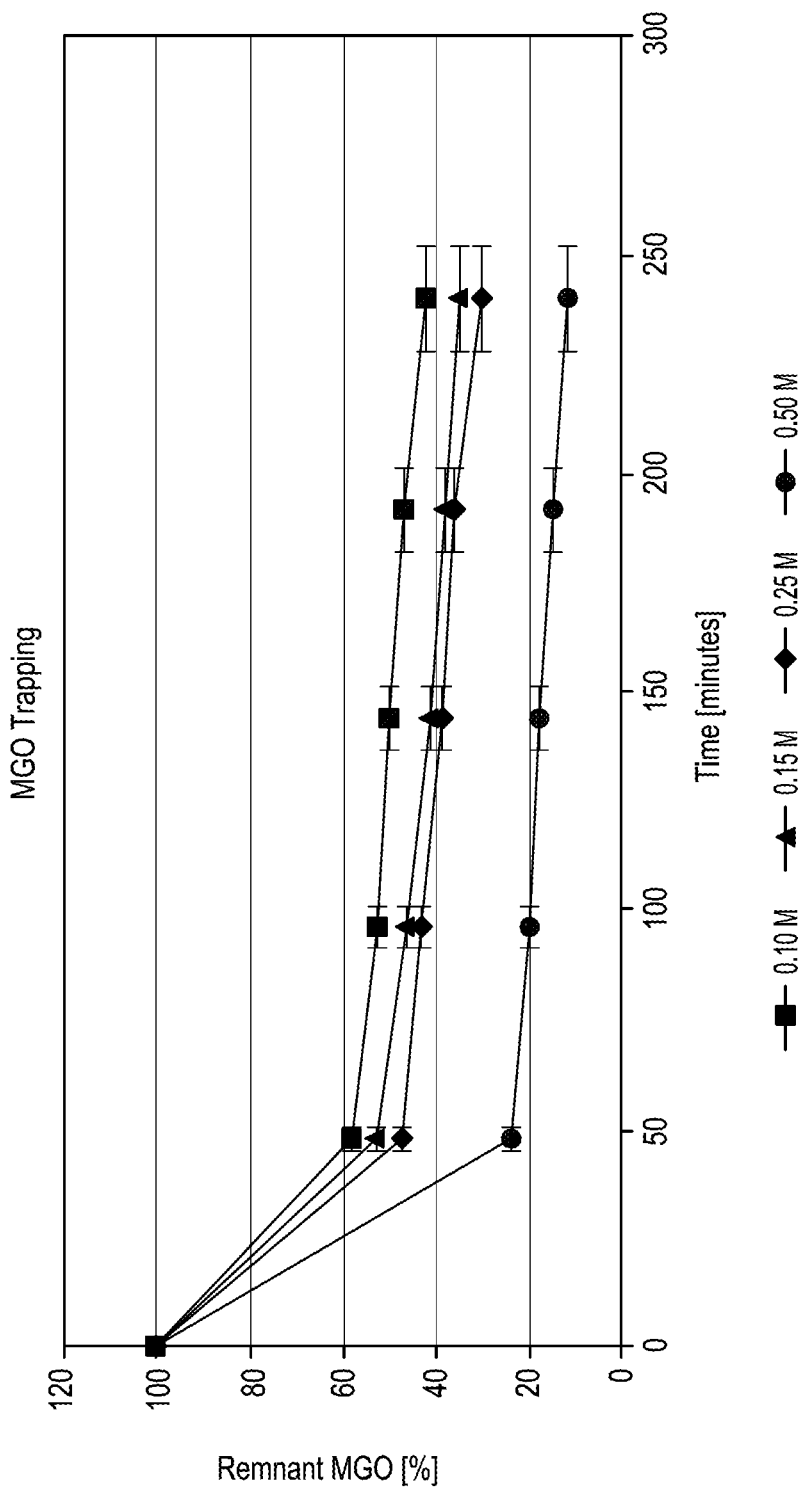
FIG. 3. Methylglyoxal trapping by different concentrations (0.10, 0.15, 0.25 and 0.50 M) of the combination of thiamine, pyridoxine, quercetin and curcumin under physiological conditions (pH 7.4 and temperature 37° C.). 0.5 M of methylglyoxal were incubated with the combination of thiamine, pyridoxine, quercetin and curcumin in a phosphate buffer solution at pH 7.4 for 48, 96, 144, 192 and 240 min.

The results shown in FIGS. 2 and 3, support the efficacy of the combination of thiamine, pyridoxine, quercetin and turmeric on the trapping of AGEs, in this case both GO and MGO under physiological conditions. More than 42% of GO and 76% of MGO were trapped within the first 48 min when the lowest molar concentration (0.10 M) of the combination of thiamine, pyridoxine, quercetin and turmeric was used and the trapping efficiency was increased to 240 min up to 70% (GO) and 88% (MGO) respectively, when the highest molar concentrations (0.50 M) of thiamine, pyridoxine, quercetin and turmeric were used. In this case, the combination trapped MGO much more efficiently than GO, when both were present in the same system. In this way, the decrease in GO and MGO concentrations favor the reduction of the damage caused by AGEs and therefore the possible reduction in the complications of diabetes (neuropathy, nephropathy and retinopathy) which are dependent on the increased levels of AGEs.

Figure 4:
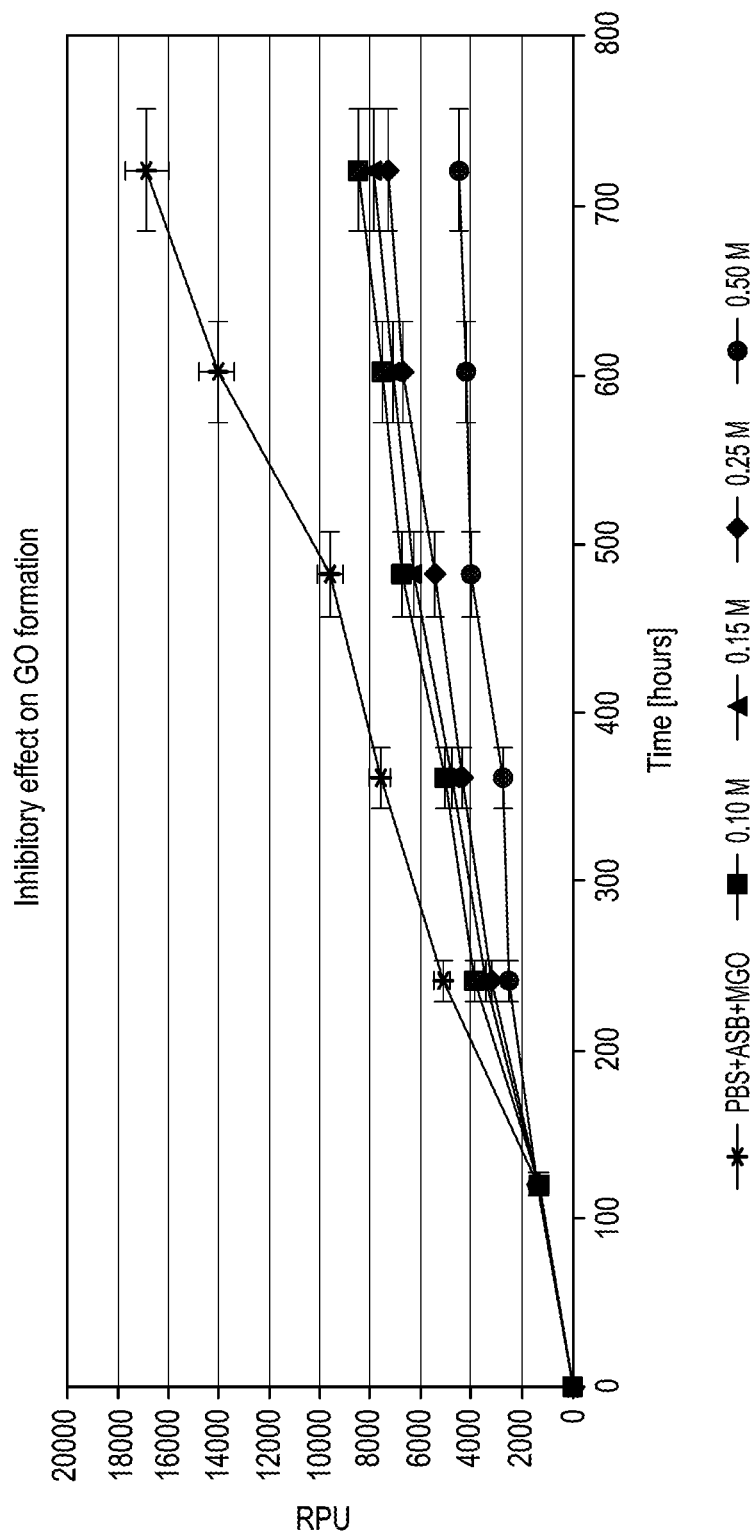
FIG. 4. Inhibitory effect of glyoxal formation by the combination of thiamine, pyridoxine, quercetin and curcumin in 4 concentrations (0.10, 0.15, 0.25 and 0.50 M), in an in vitro system with bovine serum albumin and glyoxal for 120, 240, 360, 480, 600 and 720 hours.

On the other hand, the results show that the combination of thiamine (0.10, 0.15, 0.25 and 0.5 mM), pyridoxine (0.10, 0.15, 0.25 and 0.5 mM), quercetin (0.25, 0.5, 1.5 and 2.5 mM) and turmeric (0.25, 0.5, 1.5 and 2.5 mM) significantly inhibited the formation of AGEs in the ASB-GO/MGO system (FIGS. 4 and 5). These results are consistent with the previous results, obtained on the effectiveness of the trapping of GO and MGO by the combination. At 120 hrs when the minimum inhibitory concentrations (0.10 M) of thiamine, pyridoxine, quercetin and curcumin were present in the incubation mixture, the inhibition efficiency exceeded 51% and 56% of the formation of GO and MGO, respectively. At 720 hrs in the ASB-GO and ASB-MGO system, the combination of thiamine, pyridoxine, quercetin and curcumin at concentrations of 0.50 M in the ASB-GO system, the inhibitory effect on the formation of AGEs was 73.11% and 72.48%, respectively for GO and MGO. These data indicate that the reduction of the formation of AGEs can be correlated with the decrease in damage caused by GO and MGO at the level of the retina, kidney and peripheral nerves.

These results reveal that the combination of thiamine, pyridoxine, quercetin and turmeric indeed trap GO and MGO quickly, and inhibit the formation of AGEs, probably through the formation of mono and di-GO/MGO adducts under in vitro physiological conditions.

α-Dicarbonyl compounds are known as important precursors of AGEs, which can be generated endogenously through the degradation of glucose or early glycation products. High levels of dietary fructose in the Western diet have been associated with an increase in GO and serum MGO. The results of the study show that indeed the combination of thiamine, pyridoxine, quercetin and turmeric efficiently and simultaneously trap GO and MGO under physiological conditions, when GO and MGO appear in the same system. In addition, the results show that the combination has a greater predilection for trapping MGO than GO. The reason could be that GO in aqueous solution, exists mainly as hydrated monomers, dimers or trimers, consequently free GO is slowly trapped in the reaction of the combination.

In addition, the study showed that the combination has the ability to inhibit the formation of AGEs, via GO and MGO in an ASB-GO/MGO system. The amount of AGEs decreases dramatically during the incubation time, until reaching a more marked plateau with MGO than with GO. In addition, the inhibitory activity on the formation of AGEs by the combination was greater in the ASB-MGO system than in the ASB-GO system; this may be because glycation was carried out slowly by the conversion between monomers, dimers and trimers and the free GO.

We can conclude that the combination of thiamine, pyridoxine, quercetin and turmeric is presented as an effective strategy to inhibit the formation of AGEs and prevent the processes mediated by AGEs related to various diseases.

BIBLIOGRAPHY

1. Alam M M, Ahmad I, Nassem I. Inhibitory effect of quercetin in the formation of advance glycation end products of human serum albumin: an in vitro and molecular interaction study. Int J Biol Macromol 2015; 79: 336-343.
2. Ashraf J M, Shahab U, Tabrez S, et al. Quercetin as a finder substitute to aminoguanidine in the inhibition of glycation products. Int J Biol Macromol 2015; 77: 188-192.
3. Bhuiyan M N, Mitsuhashi S, Sigetomi K, Ubukata M. Qurcetin inhibits advanced glycation end product formation via chelating metal ions, trapping methylglyoxal, and trapping reactive oxygen species. Biosci Biotechnol Biochem 2017; 81(15): 882-890.
4. Booth A A, Khalifha R G, Hudson B G. Thyamine pyrophosphate and pyridoxamine inhibit the formation of antigenic advanced glycation end-products: comparison with aminoguanidine. Biochem Biophys Res Commun 1996; 220(1): 113-119.
5. Cetin E, Civelek S, Andican G, et al. Plasma AGE-peptides and C-peptide in early-stage diabetic nephropathy patients on thiamine and pyridoxine therapy. Minerva Med 2013; 104(1): 93-101.
6. Elosta A, Ghous T, Ahmed N. Natural products as anti-glicant agents: possible therapeutic potential for diabetic complications. Curr Diabetes Rev 2012; 8(2): 92-108.
7. Engelen L, Stehouwer C D, Schalkwijk C G. Current therapeutic interventions in the glycation pathway: evidence from clinical studies. Diabetes Obes Metab 2013; 15(8): 677-689.
8. Karachalias N, Babei-Jadidi R, Kupich C, et al. High-dose thiamine therapy counters dyslipidemia and advanced glycation of plasma in streptozotocin-induced diabetic rats. Ann NY Acad Sci 2005; 1043: 777-783.
9. Kousar S, Ahmad M, Asghar M. Antiglycation activity of thiamine and benfotiamine in diabetic condition. J Pak Med Assoc 2012; 6(10): 1033-1038.
10. Li X, Zheng T, Sang S, Lv L. Quercetin inhibits advanced glycation end product formation by trapping methylglyoxal and glyoxal. J Agric Food Chem 2014; 62(50): 12152-12158.
11. Liu J P, Fong L, Zhu M M, et al. The in vitro protective effects of curcumin and demothoxycurcumin in *curcuma longa* extract on advanced glycation end products-induced mesangial cell apoptosis and oxidative stress. Plant Med 2012; 78: 1757-1760.
12. Nabavi S F, Thiagarajan R, Rastrelli L, et al Curcumin: a natural product for diabetes and its complications. Curr Top Med Chem 2015; 15(23): 2445-2455.
13. Nagai R, Shirakawa J, Ohno R, et al. Inhibition of AGEs formation by natural products. Amino Acids 2014; 46(2): 261-266.
14. Polizzi F C, Andican G, Cetin E, et al. Increased DNA-glycation in type 2 diabetic patients: the effect of thiamine and pyridoxine therapy. Exp Clin Endocrinol Diabetes 2012; 120(6): 329-334.
15. Rabbani N, Thornalley P J. Emerging role of thiamine therapy for prevention and treatment of early-stage diabetic nephropathy. Diabetes Obes Metab 2011; 13(7): 577-583.
16. Sajithlal G B, Chithra P, Chandrakasan G. Effect of curcumin on the advanced glycation and cross-linking of callagen in diabetic rats. Biochemical Pharmacology 1998; 56: 1607-1614.
17. Sun Y P, Gu J F, Tan X B, et al. Curcumin inhibits advanced glycation end products-induced oxidative stress and inflammatory responses in endothelial cell damage via trapping methylglyoxal. Mol Med Rep 2016; 13: 1475-1486.
18. Takeuchi M, Yamagishi S, Iwaki M, et al. Advanced glycation end product (age) inhibitors and their therapeutic implications in disease. Int J Clin Pharmacol Res 2004; 24(2-3): 95-101.
19. Thornalley P J. The potential role of thiamine (vitamin B1) in diabetic complications. Curr Diabetes Rev 2005; 1(3): 287-298.
20. Yamagishi S I, Matsui T, Ishibashi Y, et al. Phyochemicals against advanced glycation end products (AGEs) and receptor system. Curr Pharm Des 2017; 23(8): 1135-1141.

The invention claimed is:

1. A stable pharmaceutical, physicochemical composition, in a unit dose for the treatment of complications of diabetes mellitus induced by AGEs at micro and macrovascular level and metabolic syndrome, the composition consisting of:
   from 10 mg to 2,000 mg of Vitamin B1 group selected from thiamine hydrochloride, thiamine diphosphate, thiamine triphosphate or its pharmaceutically acceptable salts:
   from 10 mg to 2,000 mg of vitamin B6 selected from pyridoxine, pyridoxal, pyrodoxamine, pyritinol, pyrithioxin, dipyridoxolyldisulfide, pyridoxine disulfide or its pharmaceutically acceptable salts;
   from 10 mg to 2,000 mg of a flavonoid selected from quercetin or its pharmaceutically acceptable salts:
   from 10 mg to 2,000 mg of a polyphenol selected from curcumin or its pharmaceutically acceptable salts;
   at least one excipient, pharmacologically acceptable carrier, or preservative selected from the group consisting of sodium starch glycolate, microcrystalline cellulose, titanium dioxide, magnesium stearate, methylcellulose, hydroxypropyl cellulose, polyethylene glycol, polyvidone, calcium phosphate, magnesium gluconate, lactose, maltodextrin, benzoic add, salicylic add, cresol, ethyl parahydroxybenzoate, and mixtures thereof.

2. The pharmaceutical composition according to claim 1, wherein the vitamin B1 is thiamine hydrochloride.

3. The pharmaceutical composition according to claim 1, wherein the vitamin B1 is thiamine diphosphate.

4. The pharmaceutical composition according to claim 1, wherein the vitamin B1 is thiamine triphosphate.

5. The pharmaceutical composition according to claim 1, wherein the vitamin B6 is pyridoxine hydrochloride.

6. The pharmaceutical composition according to claim 1, wherein the vitamin B6 is pyridoxal phosphate.

7. The pharmaceutical composition according to claim 1, wherein the vitamin B6 is pyritinol.

8. The pharmaceutical composition according to claim 1, wherein the vitamin B6 is pyrithioxin.

9. The pharmaceutical composition according to claim 1, wherein the vitamin B6 is pyridoxamine.

10. The pharmaceutical composition according to claim 1, wherein the vitamin B6 is dipyridoxolyldisulfide.

11. The pharmaceutical composition according to claim 1, wherein the vitamin B6 is pyridoxindisulfide.

12. The pharmaceutical composition according to claim 1, wherein the vitamin B6 is an active form of pyridoxine.

13. The pharmaceutical composition according to claim 1, wherein the flavonoid is quercetin.

14. The pharmaceutical composition according to claim 1, wherein the flavonoid is quercetin-3-4'-glucoside.

15. The pharmaceutical composition according to claim 1, wherein the flavonoid is quercetin-3-galactoside.

16. The pharmaceutical composition according to claim 1, wherein the flavonoid is quercetin-3-glucoside.

17. The pharmaceutical composition according to claim 1, wherein the flavonoid is quercetin-3-rhamnoside.

18. The pharmaceutical composition according to claim 1, wherein the flavonoid is quercetin-3-rhamnoglucoside.

19. The pharmaceutical composition according to claim 1, wherein the flavonoid is quercetin-3-arabinoside.

20. The pharmaceutical composition according to claim 1, wherein the flavonoid is an active form of quercetin.

21. The pharmaceutical composition according to claim 1, wherein the polyphenol is curcumin.

22. The pharmaceutical composition according to claim 1, wherein the polyphenol is demethoxycurcumin.

23. The pharmaceutical composition according to claim 1, wherein the polyphenol is bisdemethoxycurcumin.

24. The pharmaceutical composition according to claim 1, wherein the polyphenol is an active form of curcumin.

25. The pharmaceutical composition according to claim 1 presented in an acceptable pharmaceutical form selected from the group consisting of pills, capsules, oral powders, solutions, suspensions, and emulsions.

26. The pharmaceutical composition according to claim 1 presented in a pharmaceutical form adapted for enteral administration.

27. The pharmaceutical composition according to claim 1 presented in a pharmaceutical form adapted for parenteral administration.

28. A method of using the pharmaceutical composition according to claim 1 for the treatment of complications of diabetes mellitus induced by AGEs selected from one or more of the group consisting of diabetic retinopathy, neuropathy, nephropathy, and metabolic syndrome, the method comprising administering to a patient in need thereof an effective amount of the composition.

29. A method of using the pharmaceutical composition according to claim 1 for the treatment of complications of diabetes mellitus induced by AGEs at micro and macrovascular level and metabolic syndrome, the method comprising administering to a patient in need thereof an effective amount of the composition.

* * * * *